United States Patent
Yu

(10) Patent No.: US 10,242,590 B2
(45) Date of Patent: Mar. 26, 2019

(54) WEARABLE GAIT TRAINING DEVICE AND METHOD USING THE SAME

(71) Applicant: NATIONAL YANG-MING UNIVERSITY, Taipei (TW)

(72) Inventor: Chung-Huang Yu, Taipei (TW)

(73) Assignee: NATIONAL YANG-MING UNIVERSITY, Taipei (TW)

( * ) Notice: Subject to any disclaimer, the term of this patent is extended or adjusted under 35 U.S.C. 154(b) by 591 days.

(21) Appl. No.: 14/850,136

(22) Filed: Sep. 10, 2015

(65) Prior Publication Data

US 2016/0310341 A1  Oct. 27, 2016

(30) Foreign Application Priority Data

Apr. 24, 2015 (TW) ............................. 104113192 A

(51) Int. Cl.
```
G09B 19/00      (2006.01)
G09B 5/02       (2006.01)
A61B 5/00       (2006.01)
A61B 5/11       (2006.01)
```
(52) U.S. Cl.
CPC ............ *G09B 19/003* (2013.01); *A61B 5/486* (2013.01); *A61B 5/7445* (2013.01); *G09B 5/02* (2013.01); *A61B 5/112* (2013.01); *A61B 5/6829* (2013.01); *A61B 2505/09* (2013.01); *A61B 2562/0247* (2013.01)

(58) Field of Classification Search
CPC .......... G09B 9/003; G09B 5/02; A61B 5/486; A61B 5/7445; A61B 5/112; A61B 5/6829; A61B 2505/09; A61B 2562/0247
USPC ....................................................... 434/255
See application file for complete search history.

(56) References Cited

U.S. PATENT DOCUMENTS

| | | | |
|---|---|---|---|
| 5,575,294 A * | 11/1996 | Perry | ................. A45B 3/00 362/102 |
| 6,330,888 B1 | 12/2001 | Aravantinos et al. | |
| 7,484,740 B2 | 2/2009 | Miller | |
| 8,409,116 B2 | 4/2013 | Wang et al. | |

(Continued)

FOREIGN PATENT DOCUMENTS

EP  0121026 A1 * 10/1984 ........... A43B 1/0072

OTHER PUBLICATIONS

Chung-Huang Yu et al., "Body-worn Stride Rehabilitator," International Invention and Design Competition (IIDC), Hong Kong, Dec. 4-6, 2014, pp. 1-5, 30, 31.

*Primary Examiner* — Robert P Bullington
(74) *Attorney, Agent, or Firm* — Muncy, Geissler, Olds & Lowe, P.C.

(57) ABSTRACT

A wearable training device for gait rehabilitation and a method using the same are provided. The training device includes a power supply unit, a light emitting unit, a support member and a trigger unit. The power supply unit and the light emitting unit are coupled with each other and disposed on the support member attached on a user's lower limb. The trigger unit is contacted a sole of foot of the lower limb on which the support member is attached, and coupled to the light emitting unit. When the sole of foot is landed, the trigger unit is triggered to activate the light emitting unit to project a visible light on the ground where a front stepping point of user's opposite lower limb is located, to form a stepping prompt point with visible prompt effect on the ground. Therefore, the user can be guided to step.

22 Claims, 7 Drawing Sheets

(56) References Cited

U.S. PATENT DOCUMENTS

| | | |
|---|---|---|
| 8,702,567 B2 | 4/2014 | Hu et al. |
| 2006/0025836 A1* | 2/2006 | Van Gerpen ............. A61H 3/00 607/88 |
| 2006/0292533 A1 | 12/2006 | Selod |
| 2007/0255186 A1 | 11/2007 | Grill |
| 2013/0014790 A1 | 1/2013 | Van Gerpen |
| 2013/0167888 A1 | 7/2013 | Losasso |
| 2013/0171598 A1 | 7/2013 | Losasso |
| 2016/0045386 A1* | 2/2016 | Sandler ................ A61B 5/7415 623/24 |

* cited by examiner

WEARABLE GAIT TRAINING DEVICE AND METHOD USING THE SAME

BACKGROUND OF THE INVENTION

1. Field of the Invention

The present disclosure relates to a training device, more particularly to a training device for gait rehabilitation for physically disabled person.

2. Description of the Related Art

Many diseases, such as cerebrovascular accident (CVA), Parkinson's disease and cerebral palsy, etc., cause a disabled stepping problem, so the patient's ability of daily life and life quality both are reduced efficiently. A training for gait rehabilitation is an important process for helping the physically disabled person to rebuild an alone walk ability. Clinically, a therapist must accompany and monitor the patient during existing gait training, and then judge the patient's stepping ability for further reminding the patient to walk in correct gait. However, if there is no therapist to accompany and monitor the patient, the patient possibly walks in undesirable posture in lack of reminding and further builds a wrong stepping habit, and it makes against the gait rehabilitation in future.

The documents related to gait rehabilitation training are described in following paragraph.

The U.S. Pat. No. 5,575,294, disclosed a light projecting device to project a luminous mark on the ground for instructing a physically disabled person to walk forwardly. The light projecting device is incorporated in a cane or a walking stabilizer.

The U.S. Pat. No. 7,484,740, disclosed a walking stabilizer equipped with a light projecting device to project a pattern perpendicular to the user's direction of travel for guiding a physically disabled person to walk forwardly.

The U.S. Pat. No. 8,409,116, disclosed a system equipped with a sensor (such as an accelerometer or a gyroscope) to detect whether the user's gait is smooth and regular, and when a problem of disabled action (such as freezing gait) or irregular gait is found, a wireless earphones of the system receives a signal to output a prompt voice to the user.

The U.S. Pat. No. 8,702,567, disclosed an assistive walking device equipped with a distance sensor (such as an infrared light sensor or an ultrasound sensor) to detect characteristics of a patient's gait and correspondingly provide auditory feedback to the patient for helping the patient to learn correct walk.

The US published application 20060292533, disclosed a system incorporated with a laser device and various ambulation assist devices. When the patient walks with the ambulation assist device, the laser device projects next stepping target on the ground for guiding the patient to step.

The US published application 20070255186, disclosed a walking device (such as a treadmill or a walking-assistance device) affixed with an electric eye, and a laser is projected a horizontal line onto the ground in front of the patient, to guide the patient to take larger steps during walk.

The US published application 20130014790, disclosed a walking aid installed with a light projecting device, to help the user to follow light spots in row projected on the ground during walk with the walking aid.

The US published applications 20130167888 and 20130171598, disclosed a walking aid provided with a cross bar removably attached thereunder, and the cross bar includes two balls capable of emitting light by turns to provide visible cue to guide the patient to step. During walk, if the patient's leg physically contacts the ball, a sensor inside the ball can detect vibration of the ball, and a positive feedback (such as light glowing or pleasing sound) is then outputted to indicate a successful step.

The U.S. Pat. No. 6,330,888, disclosed a cane which is equipped with a bar at a bottom end thereof. The bar can be extended to serve as a step-over indicator for the user. When the step-over indicator is not required, the bar can be withdrawn and such cane is used as a general cane.

SUMMARY OF THE INVENTION

An objective of the present disclosure is to solve problems existed in prior art.

The visible guiding step devices disclosed in these patent documents are attached at an external assistive device, such as walking aid, cane, wheelchair, etc., but they have the same drawback that the step prompt may appear disorderly and inappropriately because of change in user's action for operating assistive device. In addition, the walking aid is usually used to support and assist the physically disabled person to poise during walk, but a physically disabled person's stepping states with walking aid and without using walking aid have significant difference, so the patient's gait development may depart from the correct gait if the patient adopts the gait reminding device attached with the walking aid for a long period of time.

Some academic documents in prior art disclosed a subject-mounted light device (hereinafter, abbreviated as "SMLD") and a method of using taped step length markers to train physically disabled person. These devices and methods are departed from the walking aid, but the method of using taped step length markers may limit the training in a specific space and hard be flexibly applied to daily life. The SMLD device is attached on the chest, so the light spot projected on the ground is possibly not related to the stepping training.

In order to solve aforesaid problems, the present disclosure provides a wearable gait training device including a support member, a power supply unit, a light emitting unit, a trigger unit and a microprocessor assembly.

The support member is positioned at a physically disabled person's a sound leg, an affected leg or an attachment portion between the knee-joints and the ankle joints of two legs by a detachable manner. The position below the knee joint is defined to include the knee-joint, and the position above the ankle-joint is defined to include the ankle-joint.

The power supply unit is fixed on the support member.

The light emitting unit is positioned on the support member by a manner capable of adjusting a light projection angle, and coupled to the power supply unit. When the support member is attached on the attachment position, the visible light provided by the light emitting unit is projected to the ground where a front stepping point of the physically disabled person's opposite side leg is located, so as to form a stepping prompt point with visible prompt effect.

The trigger unit is disposed on a first landing part of the sound leg, the affected leg, or the two leg being attached with the support member, or a part of a shoe corresponding to the first landing part, and the part of the shoe includes, but not limited thereto, the interior of the shoe, the shoe sole, or the exterior of the shoe. The trigger unit is electrically connected with the light emitting unit. When the first landing part is landed, the trigger unit is triggered to send a trigger signal to activate the light emitting unit for providing the visible light. When the pressure on the first landing part disappears, triggering of the trigger unit is interrupted, so the trigger unit stops sending the trigger signal and the light emitting unit stops providing the visible light.

Moreover, the wearable gait training device of the present disclosure further includes a microprocessor assembly. The microprocessor assembly is attached on the support member and coupled with the power supply unit, the light emitting unit and the trigger unit, and the microprocessor assembly is configured for directing, controlling, instructing and managing cooperative operations between these units. The microprocessor assembly can also adjust and control the time point and duration of appearance of the stepping prompt point.

Moreover, the support member is a flexible tape which is provided with buckling structures disposed at two ends thereof, respectively, and the buckling structures can be engaged with or separated from each other. The buckling structure includes a Velcro tape, but the present disclosure not limited thereto. The support member is surrounded and positioned at the attachment position by the buckling structures.

Moreover, the support member is an elastic ring tape, and the elastic ring is surrounded and bound at the attachment position by its elasticity.

Moreover, the power supply unit includes a primary battery or a secondary battery, but the present disclosure is not limited thereto. Any current workable power supply manner can be used as the power supply unit of the present disclosure.

Moreover, the light emitting unit includes at least one laser, or at least one LED, or a laser group, or a LED group.

Moreover, the stepping prompt point can be at least one a light point, or at least one a light point group, or at least one a light pattern.

Moreover, the first landing part is a sole of rear part of the foot.

Moreover, the present disclosure further provides a gait training method applied to the wearable gait training device, and the gait training method include following steps. During a initial contact and stance phase of gait cycle of user's a foot, a stepping prompt point with visible prompt effect is projected on the ground where the front stepping point of the user's other foot should be located, and the other foot is in a terminal stance and pre-swing phase of gait cycle, and the user can refer to the stepping prompt point to lift the other leg to step on the stepping prompt point.

In the wearable gait training device of the present disclosure, the light emitting unit is attached on the specific attachment position via the support member, the trigger unit used to trigger the light emitting unit to emit the light is disposed on a first landing part of the sound leg, the affected leg, or two legs being attached with the support member, or a part of a shoe corresponding to the first landing part. The part of the shoe includes, but not limited thereto, the interior of the shoe, the shoe sole, or the exterior of the shoe. When the user's lower limb, which is worn with the wearable gait training device of the present disclosure, steps forwardly and the first landing part of the user's foot is then landed to trigger the trigger unit, the trigger unit sends a trigger signal to activate the light emitting unit, and the light emitting unit projects a visible light correspondingly to the ground where the front stepping point of the opposite side leg is located, so as to form the stepping prompt point with the visible prompt effect. The stepping prompt point can show the user a visible prompt and a stepping reference, to assist the user to step the opposite side leg on the stepping prompt point, whereby the user can be assisted to perform stepping and gait training. When the user's heel is lifted off the ground, the triggering of the trigger unit 16 is interrupted and the transmission of the trigger signal is stopped, so the light emitting unit stops providing the visible light and the stepping prompt point disappears.

The present disclosure has at least one of following effects:

The wearable gait training device of the present disclosure activates or stops the stepping prompt point according to the user's gait cycle, and adjusts the control for the stepping prompt point according to user's gait, step length, step width, step frequency, step speed or variance thereof, so that the stepping prompt can meet the user's stepping state.

The physically disabled person using or not using the walking aid, can use the wearable gait training device of the present disclosure to train stepping. The wearable gait training device of the present disclosure is attached on the user's lower limb, so the walking aid have effect on the wearable gait training device of the present disclosure totally.

The position of appearance of the stepping prompt point is determined upon the attachment position of the wearable gait training device of the present disclosure. According to the test analysis, by being attached on the attachment position as any position in the range between the knee-joint and the ankle-joint, and the range including the knee-joint and the ankle-joint, the wearable gait training device of the present disclosure can form the effective stepping prompt point on the ground where the front stepping point of the opposite side leg is located according to the user's gait cycle or variance thereof.

The position of appearance of the stepping prompt point is determined upon the attachment position of the wearable gait training device and the disposal position of the trigger unit of the present disclosure. According to the test analysis, when the attachment position is in any position in the range between the knee-joint and the ankle-joint, and the range includes the knee joint and the ankle-joint, and the trigger unit is disposed at the user's heel, the effective stepping prompt point can be formed at the ground where the front stepping point of the user's other foot at the pre-swing phase, in the initial contact state and the stance phase of the user's foot in the gait cycle. The time point of appearance of the stepping prompt point and the period of showing the stepping prompt point 15 allow the user to clearly see the stepping prompt point 15 and provide sufficient time for the user's brain to think and plan the gait continuity and smoothness and control muscle to act, so that the user can adjusts the gait according to the prompt.

The wearable gait training device of the present disclosure has a simple and light structure, so it does not cause an additional burden for the user. Each of the stepping prompts is clear, left and right step prompts are separated for easy following, and the training strength can be adjusted depended on the user's ability. The wearable gait training device of the present disclosure can be used anytime and anywhere, and not restricted by time or environment. Each step can automatically trigger and reset the prompt position, so the prompt position is not affected by the previous step.

BRIEF DESCRIPTION OF THE DRAWINGS

The detailed structure, operating principle and effects of the present disclosure will now be described in more detail hereinafter with reference to the accompanying drawings that show various embodiments of the present disclosure as follows.

DETAILED DESCRIPTION OF THE PREFERRED EMBODIMENTS

Figure 1:
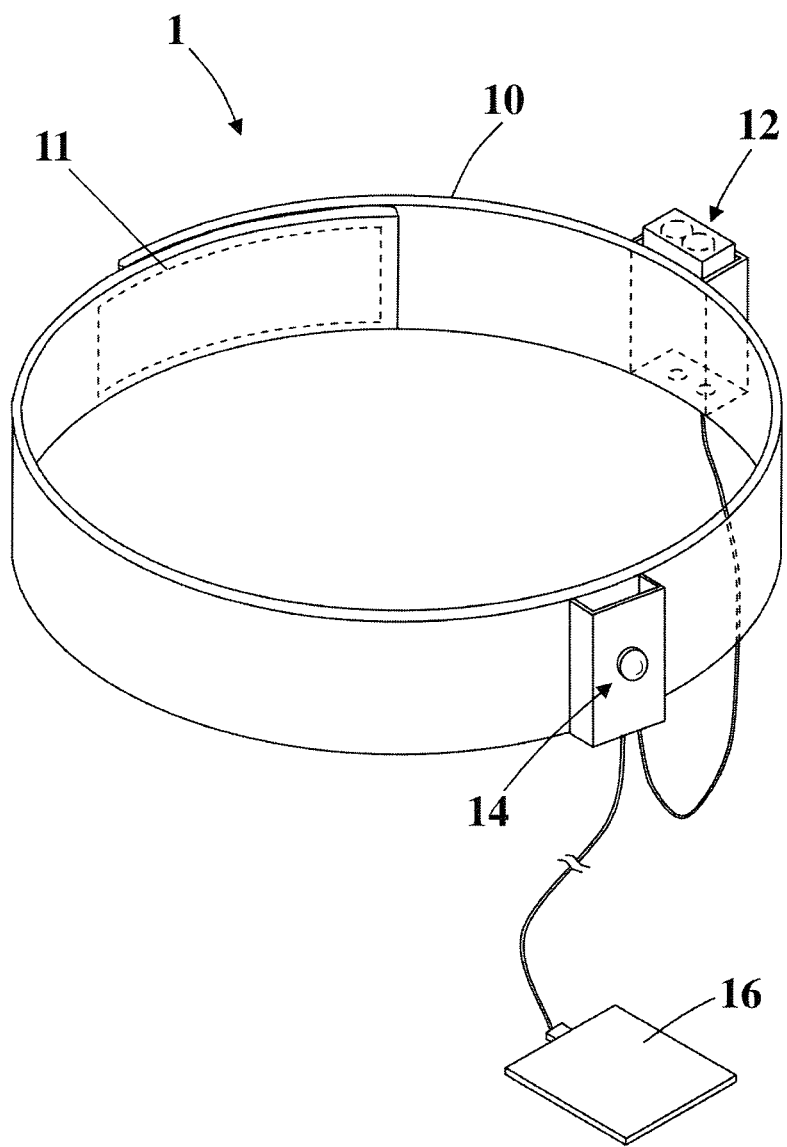
FIG. 1 is a perspective appearance view of a wearable gait training device, in accordance with the present disclosure.

Reference will now be made in detail to the exemplary embodiments of the present disclosure, examples of which are illustrated in the accompanying drawings. Therefore, it is to be understood that the foregoing is illustrative of exemplary embodiments and is not to be construed as limited to the specific embodiments disclosed, and that modifications to the disclosed exemplary embodiments, as well as other exemplary embodiments, are intended to be included within the scope of the appended claims. These embodiments are provided so that this disclosure will be thorough and complete, and will fully convey the inventive concept to those skilled in the art. The relative proportions and ratios of elements in the drawings may be exaggerated or diminished in size for the sake of clarity and convenience in the drawings, and such arbitrary proportions are only illustrative and not limiting in any way. The same reference numbers are used in the drawings and the description to refer to the same or like parts.

It will be understood that, although the terms 'first', 'second', 'third', etc., may be used herein to describe various elements, these elements should not be limited by these terms. The terms are used only for the purpose of distinguishing one component from another component. Thus, a first element discussed below could be termed a second element without departing from the teachings of embodiments. As used herein, the term "or" includes any and all combinations of one or more of the associated listed items.

Figure 2:
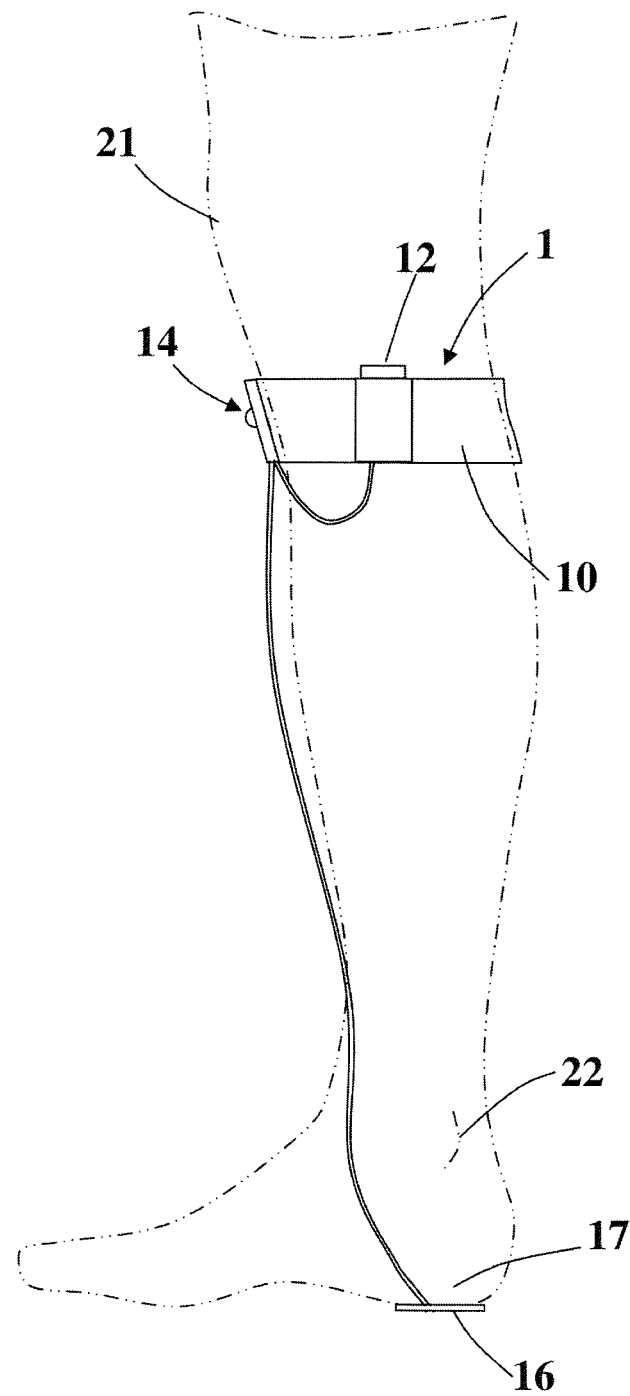
FIG. 2 is a schematic view of the wearable gait training device attached on user's lower limb, in accordance with the present disclosure.

Please refer to FIG. 1 and FIG. 2. A wearable gait training device 1 includes a support member 10, a power supply unit 12, a light emitting unit 14, a trigger unit 16 and a microprocessor assembly.

The support member 10 is positioned at a part between the knee joints 21 and the ankle-joints 22 of a physically disabled person's a sound leg, an affected leg or two legs, by a detachable manner. The position below the knee joint is defined to include the knee-joint, and the position above the ankle joint is defined to include the ankle-joint. The part to be attached by the support member 10 is defined as an attachment position. The support member 10 includes a flexible tape illustrated in the embodiment of the present disclosure, but the present disclosure not limited thereto. The support member 10 is provided with buckling structures 11 disposed at two ends thereof, respectively, and the buckling structures 11 can be engaged with or separated from each other. The buckling structure 11 includes a Velcro tape, but the present disclosure not limited thereto. The support member 10 is surrounded and positioned at the attachment position by the buckling structures 11. The support member 10 may also include an elastic ring tape (not shown in FIGs), and the elastic ring can be surrounded and bound at the attachment position by its elasticity. The descriptions of the aforesaid flexible tape and elastic ring tape indicate that the support member 10 can be adjusted according to a width of the attachment position.

The power supply unit 12 is fixed on the support member 10 by a fixation manner. The power supply unit 12 includes a primary battery or a secondary battery. Any current workable power supply manner can be used as the power supply unit of the present disclosure. In the present disclosure, any known fixation manner can be used to fix the power supply unit 12 on the support member 10. According to the embodiment of the present disclosure, a box is disposed on the support member 10 for facilitating to install or remove the power supply unit 12.

Figure 3:
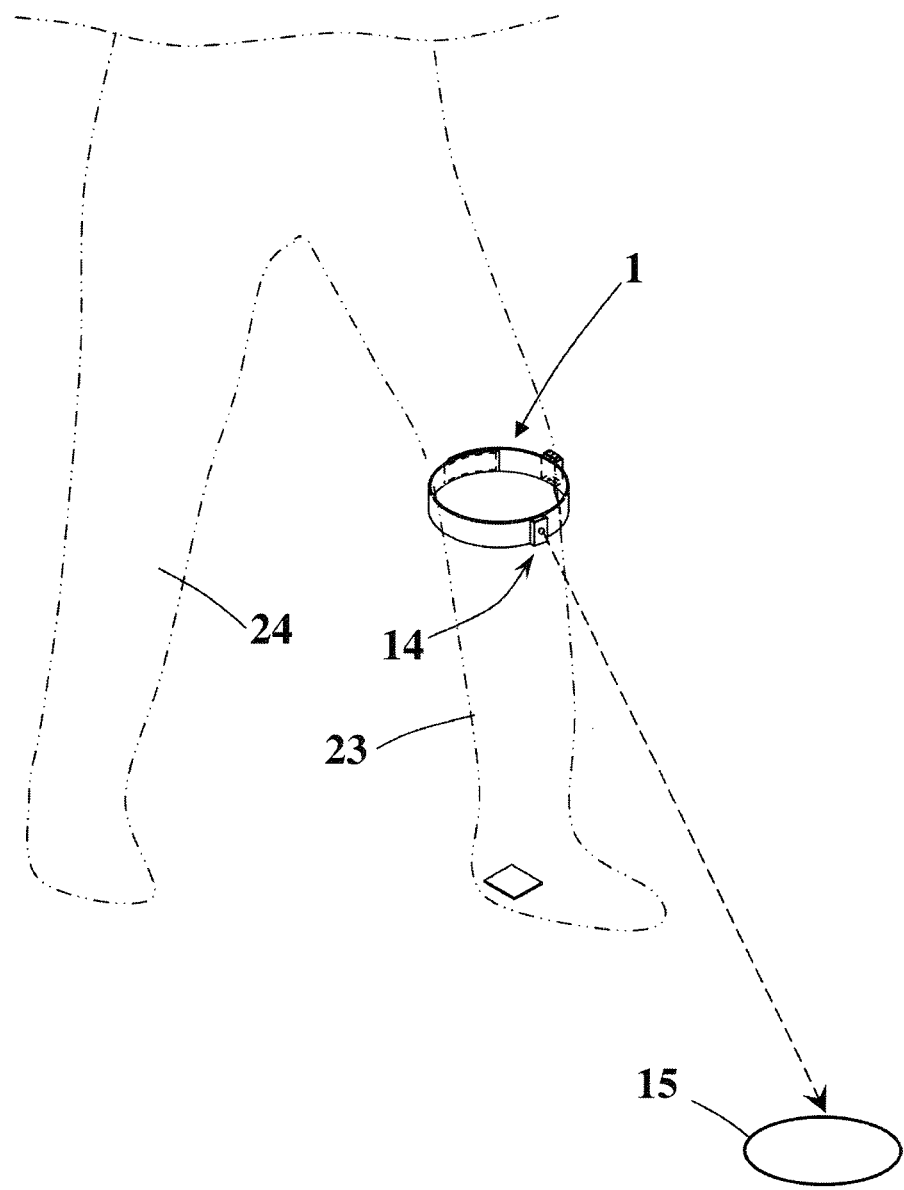
FIG. 3 is a schematic view of the wearable gait training device projecting a stepping prompt point, in accordance with the present disclosure.

The light emitting unit 14 is positioned on the support member 10 by a manner capable of adjusting a light projection angle, and coupled to the power supply unit 12. The light emitting unit 14 is configured for providing a visible light. When the support member 10 is attached on the attachment position, the visible light provided by the light emitting unit is projected to the ground where a front stepping point of the physically disabled person's opposite side leg is located, so as to form a stepping prompt point 15 with visible prompt effect, as shown in FIG. 3. The light emitting unit 14 includes at least one laser, or at least one LED, or a laser group, or a LED group. The stepping prompt point 15 can be a light point, or a light point group, or a light pattern.

The trigger unit 16 is disposed a first landing part 17 of the sound leg, the affected leg, or two legs being attached with the support member 10, or a part of a shoe corresponding thereto, and the part of the shoe includes, but not limited thereto, the interior of the shoe, the shoe sole, or the exterior of the shoe. The first landing part 17 includes, but not limited thereto, the user's sole of rear part of the foot. The trigger unit 16 may be attached at the first landing part 17 of the user's sole of foot by a tape adhesive manner, or the trigger unit 16 may be attached at a corresponding portion of the shoe by a placement manner or the tape adhesive manner. The trigger unit 16 and the light emitting unit 14 are electrically connected with each other, and the electrical connection includes wired transmission or wireless transmission. When the first landing part 17 is landed, the trigger unit 16 is triggered to send a trigger signal to activate the light emitting unit 14 for providing the visible light. When the pressure on the trigger unit 16 disappears, triggering of the trigger unit 16 is interrupted, so the trigger unit 16 stops sending the trigger signal and the light emitting unit 14 stops providing the visible light.

The wearable gait training device of the present disclosure further includes a microprocessor assembly (not shown in FIGs). The microprocessor assembly is disposed on the support member and coupled with the power supply unit, the light emitting unit and the trigger unit, and the microprocessor assembly is configured for directing, controlling, instructing and managing cooperative operations between these units.

As shown in the FIG. 3, in the wearable gait training device 1 of the present disclosure, the light emitting unit 14 is attached on the specific attachment position via the support member 10, the trigger 16 for triggering the light emitting unit 14 to emit the visible light is disposed at the at the first landing part 17 of the sound leg, affected leg, or two legs being attached with the support member, or disposed at a part of at least one shoe corresponding thereto. The part of the shoe includes, but not limited thereto, the interior of the shoe, the shoe sole, or the exterior of the shoe. When the user's lower limb, which is worn with the wearable gait training device of the present disclosure, steps forwardly to make the first landing part 17 of the user's foot be landed to trigger the trigger unit 16, the trigger unit 16 sends a trigger signal to activate the light emitting unit 14, and the light emitting unit 14 correspondingly projects a visible light to the ground where the front stepping point of the opposite side leg is located, so as to form the stepping prompt point 15 with the visible prompt effect. The stepping prompt point can show the user a visible prompt and a stepping reference, to assist the user to step the opposite side leg on the stepping prompt point 15, whereby the user can be assisted to perform stepping and gait training. When the user's first landing part 17 is lifted off the ground, the triggering of the trigger unit 16 is interrupted and the transmission of the trigger signal is stopped, so the light emitting unit 14 stops providing the visible light and the stepping prompt point 15 disappears.

As shown in the FIG. 2, the position of the stepping prompt point depends on the attachment position of the wearable gait training device of the present disclosure. According to the test analysis, if the attachment position is above the knee-joint, the projection position of the stepping prompt point 15 may exceed an acceptable stepping range for the user. If the attachment position is below the ankle-joint, wearable gait training device is too close to the ground to form the stepping prompt point on the ground where the front stepping point of the opposite side leg is located. The attachment position of the present disclosure is set in a range between the knee joint 21 and the ankle-joint 22 and including the knee-joint and the ankle-joint. In the present disclosure, the stepping prompt point 15 can be effectively formed on the ground where the front stepping point of the opposite side leg according to the user's gait cycle and gait tread, or variation thereof.

Figure 4:
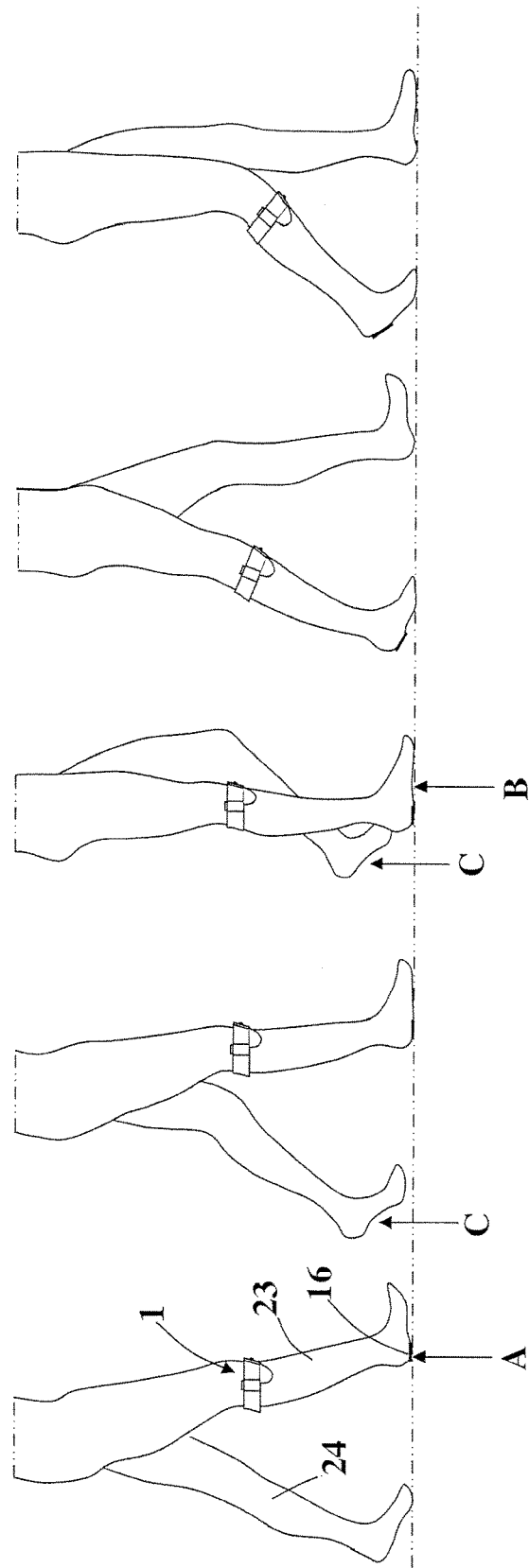
FIG. 4 is a schematic view of the wearable gait training device in cooperation with a gait cycle, in accordance with the present disclosure.

Please refer to FIG. 4, a time point of appearance of the stepping prompt point 15 also depends on the attachment position and disposal position of the trigger unit of the wearable gait training device of the present disclosure. According to the test analysis, when the trigger unit 16 is disposed at the heel, in an initial contact state A and a stance phase state B of a foot 23 in the gait cycle, the light emitting unit 14 can form an effective stepping prompt point 15 at the ground where the front stepping point of other foot 24 in lifting foot period C is located. The time point of appearance of the stepping prompt point 15 and a period of showing the stepping prompt point 15 allow the user to clearly see the stepping prompt point 15 and provide sufficient time for the user's brain to think and arrange the gait continuity and smoothness and control muscle to act, so that the user can adjust the gait according to the prompt. According to test analysis, if the stepping prompt point 15 appears too late, it causes the bearing period B of one side leg and the lifting foot period C of other side leg both are extended, so muscle of the single side leg may bear more burden, even a problem of gait unbalance may be occurred. If the stepping prompt point appears too late or the stepping prompt points for two legs appear at the same time, the user easily loses attention on the target. The stepping prompt point 15 of the present disclosure does not appear too early and cause interference, or too late and causes delay or interruption of stepping.

In the wearable gait training device of the present disclosure, the disposal position of the trigger unit can be adjusted to extend the time point of appearance of the stepping prompt point, to extend length of the stance phase B of the user's affected leg, so that the muscle strength and support strength of the user's affected leg can be trained effectively. For example, the trigger unit 16 can be disposed at the sole of fore part of the foot. In addition, the microprocessor assembly can be used to adjust and control the time point of appearance of the stepping prompt point.

The wearable gait training device of the present disclosure can be worn on the sound leg or the affected leg for different applications. When the user's affected leg cannot bear pressure sufficiently and causes the stepping distance of the sound leg be limited, the wearable gait training device of the present disclosure can be worn on the affected leg, so the stepping prompt point appears in front of the sound leg and the user can pay attention to adjust the stepping distance of the sound leg, whereby the user can train the affected leg weight bearing naturally. When the affected leg has problem of gait of drop foot or dragging gait, the wearable gait training device of the present disclosure can be worn on the sound leg, so the stepping prompt point appears in front of the affected leg, and it can guide the user to lift the affected leg to step on the stepping prompt point, whereby the user can be trained to lift the affected leg. In addition, the wearable gait training devices of the present disclosure can be worn on two legs.

To sum up, the present disclosure includes a gait training method applied to the wearable gait training device, and the gait training method include following steps. During a initial contact and stance phase of the user's one side foot in the gait cycle, the stepping prompt point with visible prompt effect is projected at the ground where the front stepping point of other side foot is located, and the other side foot is in a terminal stance and pre-swing phase of the gait cycle, so that the user can refer to the stepping prompt point to lift the other leg to step on the stepping prompt point.

Figure 5:
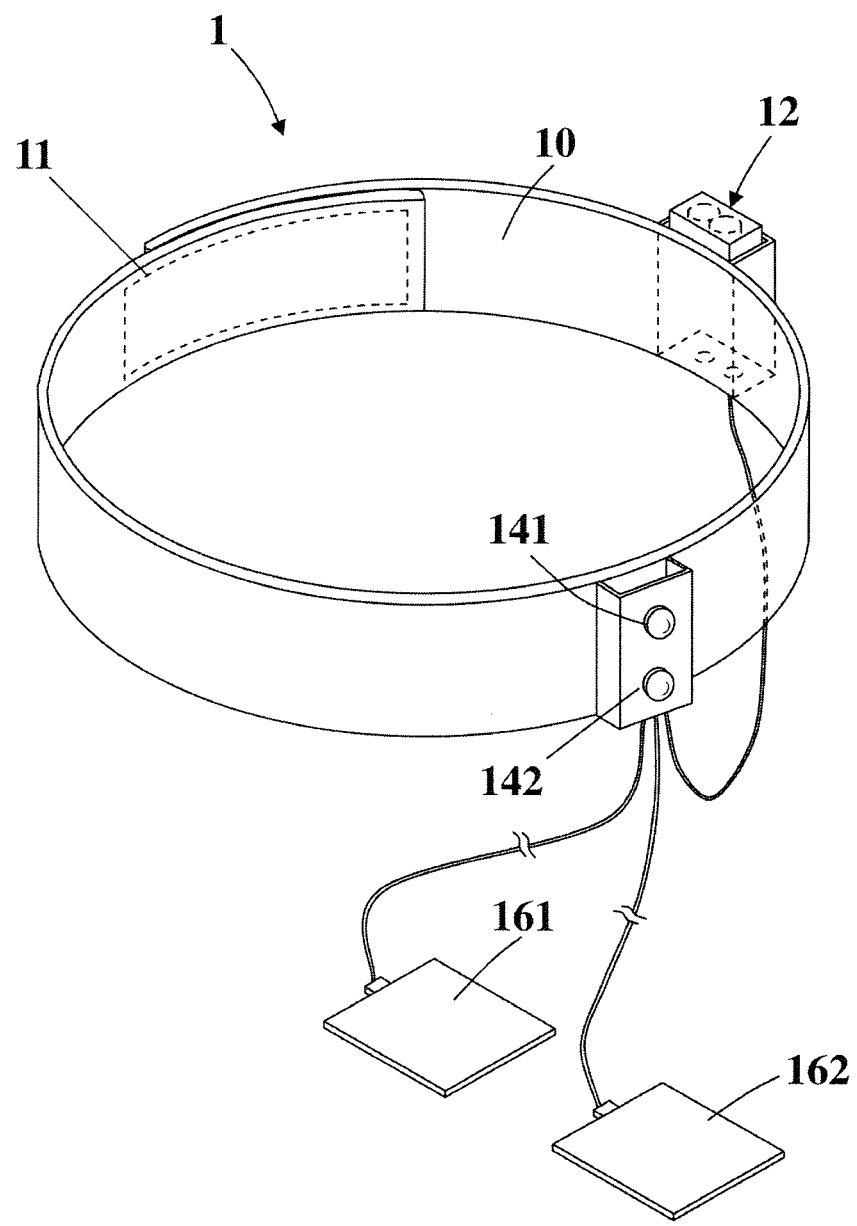
FIG. 5 is a perspective appearance view of a second embodiment of the wearable gait training device, in accordance with the present disclosure.
Figure 6:
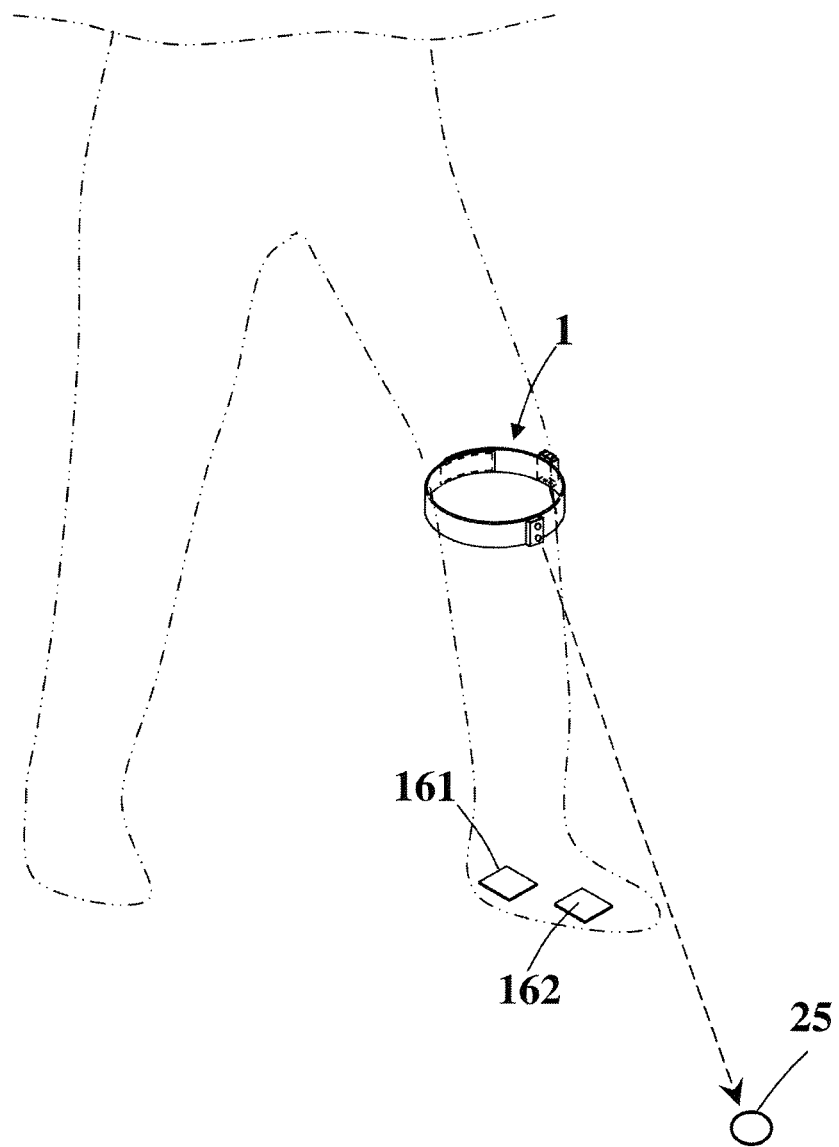
FIG. 6 is a schematic view of the second embodiment of the wearable training device projecting a heel contact prompt point, in accordance with the present disclosure.
Figure 7:
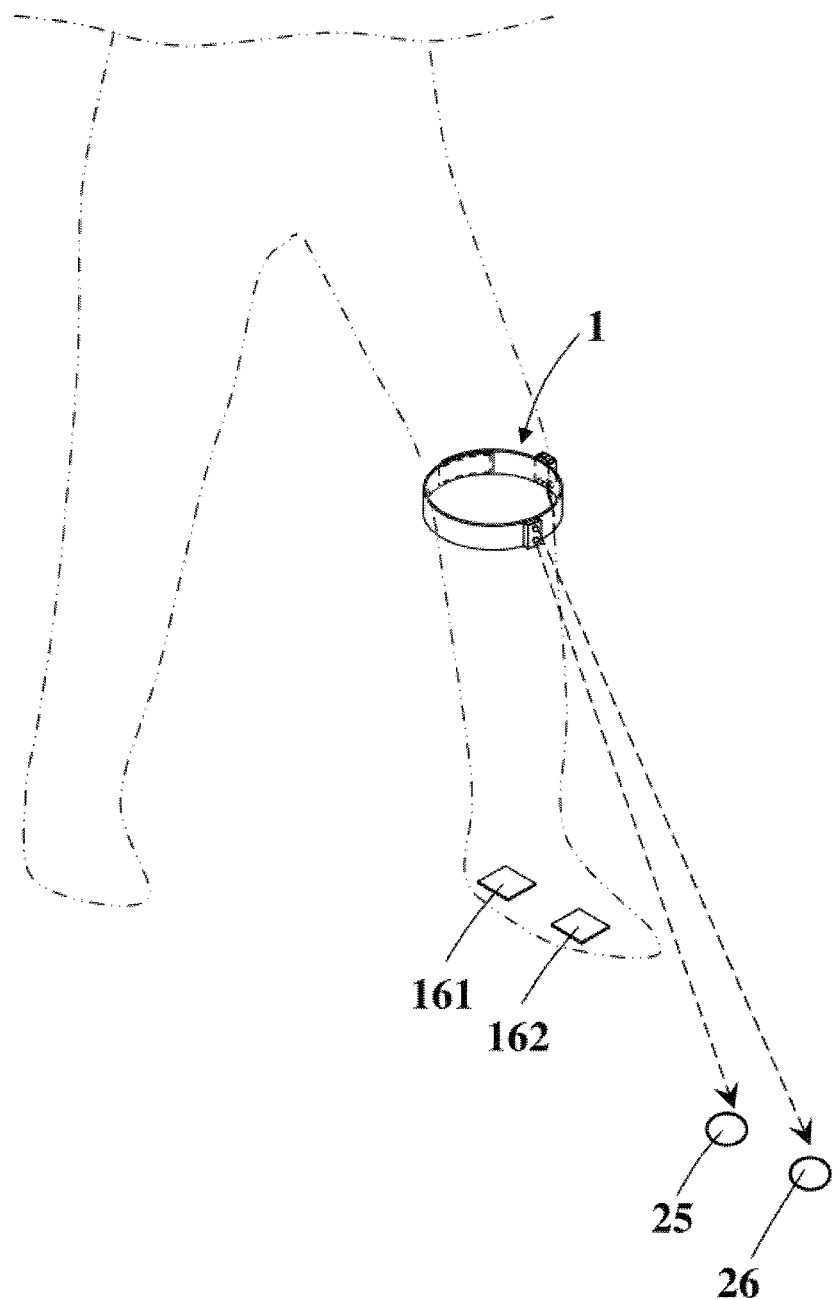
FIG. 7 is a schematic view of the second embodiment of the wearable training device projecting the heel contact prompt point and a front plantar landing prompt point, in accordance with the present disclosure.

Please refer to FIG. 5 through FIG. 7. A wearable gait training device of the present disclosure includes two trigger units (a first trigger unit 161 and a second trigger unit 162) and two light emitting unit (a first light emitting unit 141 and a second light emitting unit 142). The trigger units 161 and 162 are disposed at a sole of rear part of the foot and fore part of the foot of the sound leg, the affected leg, or both legs being attached with the support member 10, or parts of the shoe corresponding thereto, and the parts of the shoe includes, but not limited thereto, the interior of the shoe, the shoe sole, or the exterior of the shoe. The two trigger units 161 and 162 are coupled to the two light emitting units 141 and 142, respectively. While the user is stepping, the sole of rear part of the foot being landed first triggers the first trigger unit 161 to activate the first light emitting unit 142 to project a heel contact prompt point 25 on the ground where a front stepping point of the opposite side leg is located, and the sole of fore part of the foot being landed sequentially then triggers the second trigger unit 162 to activate the second light emitting unit 142 to project a front plantar landing prompt point 26 on the ground where the front stepping point of the opposite side leg is located. Two light points can be used to prompt the user the normal gait of the opposite side leg that the heel is landed first and the front plantar is then landed sequentially.

Moreover, the wearable gait training device of the present disclosure can further include a detection device and a feedback device. The detection device is used to detect whether the user completes stepping according to the stepping prompt point. If the user completes stepping according to the stepping prompt point, the detection device generates a signal to trigger the feedback device to output a reward signal, such as a pleasing bell sound, to encourage the user to continue the correct stepping practice. If the user does not complete stepping according to the stepping prompt point, the detection device generates other signal to trigger the feedback device to send a reminding signal, such as a warning sound, for reminding the user that the stepping is not complete yet.

The above-mentioned descriptions represent merely the exemplary embodiment of the present disclosure, without any intention to limit the scope of the present disclosure thereto. Various equivalent changes, alternations or modifications based on the claims of present disclosure are all consequently viewed as being embraced by the scope of the present disclosure.

What is claimed is:

1. A wearable gait training device, comprising:
    a support member, positioned at an attachment position of a user's lower limb by a detachable manner;
    a power supply unit, fixed on the support member;
    a light emitting unit, configured for providing a visible light, and positioned on the support member by a manner capable of adjusting a light projection angle, and coupled to the power supply unit, in a case that the support member is attached at the attachment position, the visible light provided by the light emitting unit being projected to a ground where a front stepping point for a user's opposite lower limb is located, so as to form a stepping prompt point;
    a trigger unit, contacted a sole of foot to which the support member is attached, and electrically connected to the light emitting unit, wherein in the case that the sole of foot is landed, the trigger unit activates the light emitting unit to provide the visible light, and in the case that a pressure on the sole of foot disappears, triggering of the trigger unit is interrupted and the light emitting unit is stopped providing the visible light, and a disposal position of the trigger unit is adjusted to extend a time point of appearance of the stepping prompt point.

2. The wearable gait training device as defined in claim 1, further comprising a microprocessor assembly which is disposed on the support member and coupled to the power supply unit, the light emitting unit and the trigger unit.

3. The wearable gait training device as defined in claim 1, further comprising a detection device and a feedback device, wherein in a case that the user completes stepping according to the stepping prompt point, the detection device generates a signal to trigger the feedback device to output a reward signal, and in a case that the user does not complete stepping according to the stepping prompt point, the detection device generates an other signal to trigger the feedback device to send a reminding signal.

4. The wearable gait training device as defined in claim 1, wherein the attachment position is any position between a knee joint and an ankle-joint of the user's lower limb, a position below the knee-joint comprises the knee-joint, and a position above the ankle-joint comprises the ankle-joint.

5. The wearable gait training device as defined in claim 1, wherein the trigger unit is disposed at a sole of fore part of the foot.

6. The wearable gait training device as defined in claim 1, wherein the trigger unit is disposed at a sole of rear part of the foot.

7. The wearable gait training device as defined in claim 1, wherein the trigger unit is disposed at least one shoe worn with the user's lower limb.

8. The wearable gait training device as defined in claim 1, wherein the support member is a flexible tape which is provided with buckling structures at two ends thereof respectively, and the buckling structures can be engaged with or separated from each other.

9. The wearable gait training device as defined in claim 1, wherein the light emitting unit comprises a laser, a LED, or a combination thereof.

10. The wearable gait training device as defined in claim 1, wherein the stepping prompt point comprises a light point, a light point group, a light pattern or a combination thereof.

11. The wearable gait training device as defined in claim 2, wherein the microprocessor assembly is used to adjust and control the time point of appearance of the stepping prompt point.

12. A gait training method applied to the wearable gait training device as defined in claim 1, the gait training method comprising:
    during initial contact and stance phase of gait cycle, projecting the stepping prompt point with visible prompt effect on the ground where the front stepping point of a user's other foot is located, wherein the user's other foot is in terminal stance and pre-swing phase in the gait cycle, and the user can refer to the stepping prompt point to lift the user's other foot to step on the stepping prompt point.

13. A wearable gait training device, comprising:
    a support member, positioned at an attachment position of a user's lower limb by a detachable manner;
    a power supply unit, fixed on the support member;
    two light emitting units, configured for providing a visible light respectively, and positioned on the support member by a manner capable of adjusting a light projection angle, and coupled to the power supply unit, respectively, and in a case that the support member is attached at the attachment position, the visible light provided by the light emitting unit being projected to a ground where a front stepping point of a user's opposite lower limb is located, wherein one of the two light emitting units forms a heel contact prompt point on the ground, and other of the two light emitting units forms a front plantar landing prompt point on the ground;
    two trigger units, contacted a sole of foot of a lower limb to which the support member is attached, and electrically connected to the two light emitting units, respectively, and in the case that the foot is landed, the two trigger units activating the two light emitting units to provide the visible light, respectively, and in the case that a pressure on a sensor placed at the sole of foot disappears, triggering of the trigger unit being interrupted and the light emitting unit being stopped providing the visible light, and a disposal position of the two trigger units is adjusted to extend a time point of appearance of the stepping prompt point.

14. The wearable gait training device as defined in claim 13, further comprising a microprocessor assembly which is disposed on the support member and coupled to the power supply unit, the light emitting unit and the trigger unit.

15. The wearable gait training device as defined in claim 13, further comprising a detection device and a feedback device, wherein in a case that the user completes stepping according to the stepping prompt point, the detection device generates a signal to trigger the feedback device to output a reward signal, and in a case that the user does not complete stepping according to the stepping prompt point, the detection device generates an other signal to trigger the feedback device to send a reminding signal.

16. The wearable gait training device as defined in claim 13, wherein the attachment position is any position between a knee-joint and an ankle joint of the user's limb, a position below the knee-joint comprises the knee-joint, and a position above the ankle joint comprises the ankle-joint.

17. The wearable gait training device as defined in claim 13, wherein the two trigger units are disposed at a sole of rear part of the foot and a fore part of the foot, respectively.

18. The wearable gait training device as defined in claim 17, wherein the two trigger units are disposed on shoes corresponding to the sole of rear part of the foot and the sole of fore part of the foot, respectively.

19. The wearable gait training device as defined in claim 13, wherein the support member is a flexible tape which is provided with buckling structures at two ends thereof respectively, and the buckling structures can be engaged with or separated from each other.

20. The wearable gait training device as defined in claim 13, wherein the light emitting unit comprises a laser, a LED, or a combination thereof.

21. The wearable gait training device as defined in claim 13, wherein the heel contact prompt point or a sole of fore part of the foot landing prompt point comprises a light point, a light point group, a light pattern or a combination thereof.

22. A gait training method applied to the wearable gait training device as defined in claim 13, the gait training method comprising:
   during initial contact and stance phase of user's foot in gait cycle, projecting the heel contact prompt point and a sole of fore part of the foot landing prompt point with visible prompt effect at the ground where a front stepping point of other foot is located, and the other foot in the terminal stance and pre-swing phase in the gait cycle, so that the user can refer to the stepping prompt point to lift the other leg to step the user's heel on the landing prompt point first and then step the user's front plantar on the front plantar landing prompt point sequentially.

* * * * *